(12) United States Patent
Mestek et al.

(10) Patent No.: US 11,478,155 B2
(45) Date of Patent: *Oct. 25, 2022

(54) HYPOVOLEMIA DIAGNOSIS TECHNIQUE

(71) Applicant: Covidien LP, Mansfield, MA (US)

(72) Inventors: Michael Mestek, Superior, CO (US); Daniel Lisogurski, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 973 days.

This patent is subject to a terminal disclaimer.

(21) Appl. No.: 16/133,317

(22) Filed: Sep. 17, 2018

(65) Prior Publication Data

US 2019/0014992 A1 Jan. 17, 2019

Related U.S. Application Data

(60) Division of application No. 14/509,302, filed on Oct. 8, 2014, now Pat. No. 10,092,193, which is a (Continued)

(51) Int. Cl.
*A61B 6/00* (2006.01)
*A61B 5/02* (2006.01)
(Continued)

(52) U.S. Cl.
CPC ........ *A61B 5/02042* (2013.01); *A61B 5/0205* (2013.01); *A61B 5/029* (2013.01); (Continued)

(58) Field of Classification Search
CPC .............. A61B 5/02042; A61B 5/0205; A61B 5/02405; A61B 5/02427; A61B 5/0261; (Continued)

(56) References Cited

U.S. PATENT DOCUMENTS

| 4,802,486 A | 2/1989 | Goodman et al. |
| 4,807,630 A | 2/1989 | Malinouskas |

(Continued)

FOREIGN PATENT DOCUMENTS

| EP | 0734221 | 6/1995 |
| JP | 10216113 | 8/1998 |

(Continued)

OTHER PUBLICATIONS

Addison, "The Illustrated Wavelet Transform Handbook—Introductory Theory and Applications in Science, Engineering, Medicine and Finance," Institute of Physics Publishing, IOP Publishing Ltd., Jul. 15, 2002, 69 pp.

(Continued)

*Primary Examiner* — Baisakhi Roy
(74) *Attorney, Agent, or Firm* — Shumaker & Sieffert, P.A.

(57) ABSTRACT

Embodiments of the present disclosure relate to a system and method for determining a risk, onset, or presence of hypovolemia based on one or more features of a plethysmographic waveform during a patient breathing cycle. For example, a hypovolemic patient may exhibit characteristic changes in pulse amplitude or stroke volume during inhalation and exhalation relative to a healthy patient. Further, a trend or pattern of such features may be used to assess the patient's fluid condition.

24 Claims, 8 Drawing Sheets

Related U.S. Application Data continuation of application No. 13/404,402, filed on Feb. 24, 2012, now Pat. No. 8,880,155.

(51) Int. Cl.
| | |
|---|---|
| *A61B 5/1455* | (2006.01) |
| *A61B 5/0205* | (2006.01) |
| *A61B 5/026* | (2006.01) |
| *A61B 5/029* | (2006.01) |
| *A61B 5/0295* | (2006.01) |
| *A61B 5/00* | (2006.01) |
| *A61B 5/024* | (2006.01) |
| *A61B 5/08* | (2006.01) |

(52) U.S. Cl.
CPC .......... *A61B 5/0261* (2013.01); *A61B 5/0295* (2013.01); *A61B 5/14551* (2013.01); *A61B 5/4848* (2013.01); *A61B 5/7203* (2013.01); *A61B 5/726* (2013.01); *A61B 5/7246* (2013.01); *A61B 5/7275* (2013.01); *A61B 5/7278* (2013.01); *A61B 5/7282* (2013.01); *A61B 5/742* (2013.01); *A61B 5/746* (2013.01); *A61B 5/02405* (2013.01); *A61B 5/02427* (2013.01); *A61B 5/0816* (2013.01)

(58) Field of Classification Search
CPC ............ A61B 5/14551; A61B 5/02416; A61B 5/0816; A61B 5/726; A61B 5/6814; A61B 5/6826; A61B 5/6816; A61B 5/6838

See application file for complete search history.

(56) References Cited

U.S. PATENT DOCUMENTS

| | | | |
|---|---|---|---|
| 4,911,167 A | 3/1990 | Corenman et al. | |
| 4,928,692 A | 5/1990 | Goodman et al. | |
| 4,934,372 A | 6/1990 | Corenman et al. | |
| 4,972,331 A | 11/1990 | Chance | |
| 5,122,974 A | 6/1992 | Chance | |
| 5,273,036 A | 12/1993 | Kronberg et al. | |
| RE35,122 E | 12/1995 | Corenman et al. | |
| 6,129,675 A * | 10/2000 | Jay | A61B 5/0205 600/323 |
| 6,325,761 B1 | 12/2001 | Jay | |
| 6,361,501 B1 | 3/2002 | Amano et al. | |
| 6,393,311 B1 | 5/2002 | Edgar, Jr. et al. | |
| 6,398,727 B1 | 6/2002 | Bui et al. | |
| 6,519,486 B1 | 2/2003 | Edgar, Jr. et al. | |
| 6,650,918 B2 | 11/2003 | Terry | |
| 6,654,623 B1 | 11/2003 | Kästle | |
| 6,658,277 B2 | 12/2003 | Wasserman | |
| 6,702,752 B2 | 3/2004 | Dekker | |
| 6,709,402 B2 | 3/2004 | Dekker | |
| 6,773,397 B2 | 8/2004 | Kelly | |
| 6,839,581 B1 | 1/2005 | El-Solh et al. | |
| 6,850,787 B2 | 2/2005 | Weber et al. | |
| 6,896,661 B2 | 5/2005 | Dekker | |
| 6,990,426 B2 | 1/2006 | Yoon et al. | |
| 7,001,337 B2 | 2/2006 | Dekker | |
| 7,139,599 B2 | 11/2006 | Terry | |
| 7,171,251 B2 | 1/2007 | Sarussi et al. | |
| 7,344,497 B2 | 3/2008 | Kline | |
| 7,373,194 B2 | 5/2008 | Weber et al. | |
| 7,421,296 B1 | 9/2008 | Benser et al. | |
| 8,128,569 B1* | 3/2012 | Mason | A61B 5/0205 600/484 |
| 8,485,978 B2* | 7/2013 | Linder | A61B 5/6826 600/481 |
| 8,880,155 B2* | 11/2014 | Mestek | A61B 5/02042 600/479 |
| 10,092,193 B2 | 10/2018 | Mestek et al. | |
| 2002/0032386 A1* | 3/2002 | Sackner | A61B 5/0205 600/536 |
| 2003/0163054 A1 | 8/2003 | Dekker | |
| 2003/0236647 A1 | 12/2003 | Yoon et al. | |
| 2004/0010188 A1 | 1/2004 | Wasserman | |
| 2004/0039273 A1 | 2/2004 | Terry | |
| 2004/0044276 A1* | 3/2004 | Arnold | A61B 5/14551 600/323 |
| 2004/0087846 A1 | 5/2004 | Wasserman | |
| 2004/0171948 A1 | 9/2004 | Terry | |
| 2004/0204636 A1 | 10/2004 | Diab et al. | |
| 2005/0049470 A1 | 3/2005 | Terry | |
| 2005/0222502 A1 | 10/2005 | Cooper | |
| 2005/0234357 A1* | 10/2005 | Xue | A61B 5/35 600/510 |
| 2006/0211930 A1 | 9/2006 | Scharf et al. | |
| 2006/0282001 A1 | 12/2006 | Noel et al. | |
| 2007/0049974 A1* | 3/2007 | Li | A61B 5/363 607/4 |
| 2007/0149871 A1 | 6/2007 | Sarussi et al. | |
| 2007/0255146 A1* | 11/2007 | Andrews | A61B 5/02416 600/508 |
| 2007/0293746 A1 | 12/2007 | Sarussi et al. | |
| 2008/0076988 A1 | 3/2008 | Sarussi et al. | |
| 2008/0076990 A1 | 3/2008 | Sarussi et al. | |
| 2008/0200775 A1* | 8/2008 | Lynn | A61B 5/366 600/301 |
| 2008/0262326 A1 | 10/2008 | Hete et al. | |
| 2008/0269626 A1* | 10/2008 | Gallagher | A61B 5/02416 600/509 |
| 2010/0069761 A1* | 3/2010 | Karst | A61B 5/0806 600/484 |
| 2010/0081942 A1* | 4/2010 | Huiku | A61M 5/1723 600/483 |
| 2010/0099964 A1 | 4/2010 | O'Reilly et al. | |
| 2010/0106030 A1* | 4/2010 | Mason | A61B 5/025 600/493 |
| 2010/0249559 A1* | 9/2010 | Lovejoy | A61B 5/02028 600/364 |
| 2010/0324827 A1* | 12/2010 | Addison | A61B 5/14551 702/19 |
| 2011/0077474 A1* | 3/2011 | Huiku | A61B 5/4875 600/301 |
| 2011/0087115 A1 | 4/2011 | Sackner et al. | |
| 2011/0257549 A1* | 10/2011 | Wysocki | A61M 16/024 600/529 |
| 2011/0301436 A1* | 12/2011 | Teixeira | A61B 5/14552 600/301 |
| 2012/0172688 A1 | 7/2012 | Mason et al. | |
| 2012/0302905 A1* | 11/2012 | Kaski | A61B 5/7221 600/513 |
| 2013/0006075 A1* | 1/2013 | Baker, Jr. | A61M 16/0051 600/322 |
| 2013/0146056 A1* | 6/2013 | Baker, Jr. | A61M 16/0057 128/204.23 |

FOREIGN PATENT DOCUMENTS

| | | |
|---|---|---|
| JP | 2005034472 | 2/2005 |
| JP | 3115374 | 12/2005 |
| WO | 9843071 | 10/1998 |
| WO | 0021438 | 4/2000 |
| WO | 0176471 | 10/2001 |
| WO | 03000125 | 1/2003 |
| WO | 03039326 | 5/2003 |
| WO | 2004075746 | 9/2004 |
| WO | 2006067725 | 6/2006 |

OTHER PUBLICATIONS

Prosecution History from U.S. Appl. No. 13/404,402, dated Sep. 26, 2013 through Jul. 2, 2014, 50 pp.

Prosecution History from U.S. Appl. No. 14/509,302, dated Jul. 19, 2017 through Jul. 30, 2018, 85 pp.

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18, 2004.

(56) References Cited

OTHER PUBLICATIONS

Barnum, P.T., et al.; "Novel Pulse Oximetry Technology Capable of Reliable Bradycardia Monitoring in the Neonate," Respiratory Care, vol. 42, No. 1, p. 1072, Nov. 1997.
Barreto, Armando B., et al.; "Adaptive LMS Delay Measurement in dual Blood Volume Pulse Signals for Non-Invasive Monitoring," IEEE, pp. 117-120, 1997.
Belal, Suliman Yousef, et al.; "A fuzzy system for detecting distorted plethysmogram pulses in neonates and paediatric patients," Physiol. Meas., vol. 22, pp. 397-412 (2001).
Chan, K.W., et al.; "17.3: Adaptive Reduction of Motion Artifact from Photoplethysmographic Recordings using a Variable Step-Size LMS Filter," IEEE, pp. 1343-1346 (2002).
Chen, Liangyou, et al.; "IS respiration-induced variation in the photoplethysmogram associated with major hypovolemia in patients with actue tramatic injuries," Shock, vol. 34, No. 5, pp. 455-460, 2010.
Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.
Crespi, F., et al.; "Near infrared oximeter prototype for non-invasive analysis of rat brain oxygenation," Optical Sensing, Proceedings of SPIE, vol. 5459, pp. 38-45, 2004.
Cubeddu, Rinaldo, et al.; "Portable 8-channel time-resolved optical imager for functional studies of biological tissues," Photon Migration, Optical Coherence Tomography, and Microscopy, Proceedings of SPIE, vol. 4431, pp. 260-265, 2001.
Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.
Cysewska-Sobusaik, Anna; "Metrological Problems With noninvasive Transillumination of Living Tissues," Proceedings of SPIE, vol. 4515, pp. 15-24, 2001.
Earthrowl-Gould, T., et al.; "Chest and abdominal surface motion measurement for continuous monitoring of respiratory function," Proc. Instn Mech Engrs, V215, Part H; pp. 515-520, 2001.
East, Christine E., et al.; "Fetal Oxygen Saturation and Uterine Contractions During Labor," American Journal of Perinatology, vol. 15, No. 6, pp. 345-349 (Jun. 1998).
Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.
Gesquiere, Michael J., et al., "Impact of withdrawal of 450 ML of blook on respiration-induced oscillations of the ear plethysmographic waveform," Journal of Clinical Monitoring and Computing, 21:277-282, 2007.
Goldman, Julian M.; "Masimo Signal Extraction Pulse Oximetry," Journal of Clinical Monitoring and Computing, vol. 16, pp. 475-483 (2000).
Hamilton, Patrick S., et al.; "Effect of Adaptive Motion-Artifact Reduction on QRS Detection," Biomedical Instrumentation & Technology, pp. 197-202, May-Jun. 2000.
Huang, J., et al.; "Low Power Motion Tolerant Pulse Oximetry," Anesthesia & Analgesia 2002 94:S103.
Johansson, A.; "Neural network for photoplethysmographic respiratory rate monitoring," Medical & Biological Engineering & Computing, vol. 41, pp. 242-248, 2003.
Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.
Kaestle, S.; "Determining Artefact Sensitivity of New Pulse Oximeters in Laboratory Using Signals Obtained from Patient," Biomedizinische Technik, vol. 45, 2000.
Kim, J.M., et al.; "Signal Processing Using Fourier & Wavelet Transform for pulse oximetry," pp. II-310-II-311, 2001.

Leahy, Martin J., et al.; "Sensor Validation in Biomedical Applications," IFAC Modelling and Control in Biomedical Systems, Warwick, UK; pp. 221-226, 1997.
Liu, Ying, et al.; "Sensor design of new type reflectance pulse oximetry," Optics in Health Care and Biomedical Optics: Diagnostics and Treatment, Proceedings of SPIE, vol. 4916, pp. 98-102, 2002.
Lopez-Silva, Sonnia Maria Lopez, et al.; "Near-infrared transmittance pulse oximetry with laser diodes," Journal of Biomedical Optics, vol. 8, No. 3, pp. 525-533, Jul. 2003.
Lopez-Silva, Sonnia Maria Lopez, et al.; "NIR transmittance pulse oximetry system with laser diodes," Clinical Diagnostic Systems, Proceedings of SPIE, vol. 4255, pp. 80-87, 2001.
Lutter, N., et al.; "Comparison of Different Evaluation Methods for a Multi-wavelength Pulse Oximeter," Biomedizinische Technik, vol. 43, 1998.
Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293, 2001.
Mannheimer, Paul D., et al.; "Wavelength Selection for Low-Saturation Pulse Oximetry," IEEE Transactions on Biomedical Engineering, vol. 44, No. 3, pp. 148-158, Mar. 1997.
McGrath, S.P., et al.; "Pulse oximeter plethysmographic waveform changes in awake, spontaneously breathing, hypovolemic volunteers," Anesth. Analg. vol. 112 No. 2, pp. 368-374, 2010.
Neumann, R., et al.; "Fourier Artifact suppression Technology Provides Reliable SpO2,," Anesthesia & Analgesia, 2002, 94: S105.
Nilsson, Lena, et al.; "Monitoring of Respiratory Rate in Postoperative Care Using a New Photoplethysmographic Technique," Journal of Clinical Monitoring and Computing, vol. 16, pp. 309-315, 2000.
Nogawa, Masamichi, et al.; "A Novel Hybrid Reflectance Pulse Oximater Sensor with improved Linearity and General Applicability to Various Portions of the Body," Proceedings of the 20th Annual International Conference of the IEEE Engineering in Medicine and Biology, vol. 20, 1997.
Odagriri, Y.; "Pulse Wave Measuring Device," Micromechatronics, vol. 42, No. 3, pp. 6-11, published Sep. 1998.
Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.
Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.
Seelbach-Gobel, Birgit, et al.; "The prediction of fetal acidosis by means of intrapartum fetal pulse oximetry," Am J. Obstet. Gynecol., vol. 180, No. 1, Part 1, pp. 73-81, 1999.
Shamir, M., et al.; "Pulse oximetry plethysmographic waveform during changes in blood volume," British Journal of Anaesthesia 82(2): 178-81, 1999.
Spigulis, Janis, et al.; "Optical multi-channel sensing of skin blood pulsations," Optical Sensing, Proceedings of SPIE, vol. 5459, pp. 46-53M, 2004.
Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.
Such, Hans Olaf; "Optoelectronic Non-invasive Vascular Diagnostics Using multiple Wavelength and Imaging Approach," Dissertation, Jun. 19, 1998.
Todd, Bryan, et al.; "The Identification of Peaks in Physiological Signals," Computers and Biomedical Research, vol. 32, pp. 322-335, 1999.
Wu, Dongmei, et al.; "Na*/H* Exchange inhibition delays the onset of hypovolemic circulatory shock in pigs," Shock, vol. 29, No. 4, pp. 519-525, 2008.
Yoon, Gilwon, et al.; "Multiple diagnosis based on Photoplethysmography: hematocrit, SpO2, pulse and respiration," Optics

(56) References Cited

OTHER PUBLICATIONS in Health Care and Biomedical optics: Diagnostics and Treatment; Proceedings of the SPIE, vol. 4916; pp. 185-188, 2002.

* cited by examiner

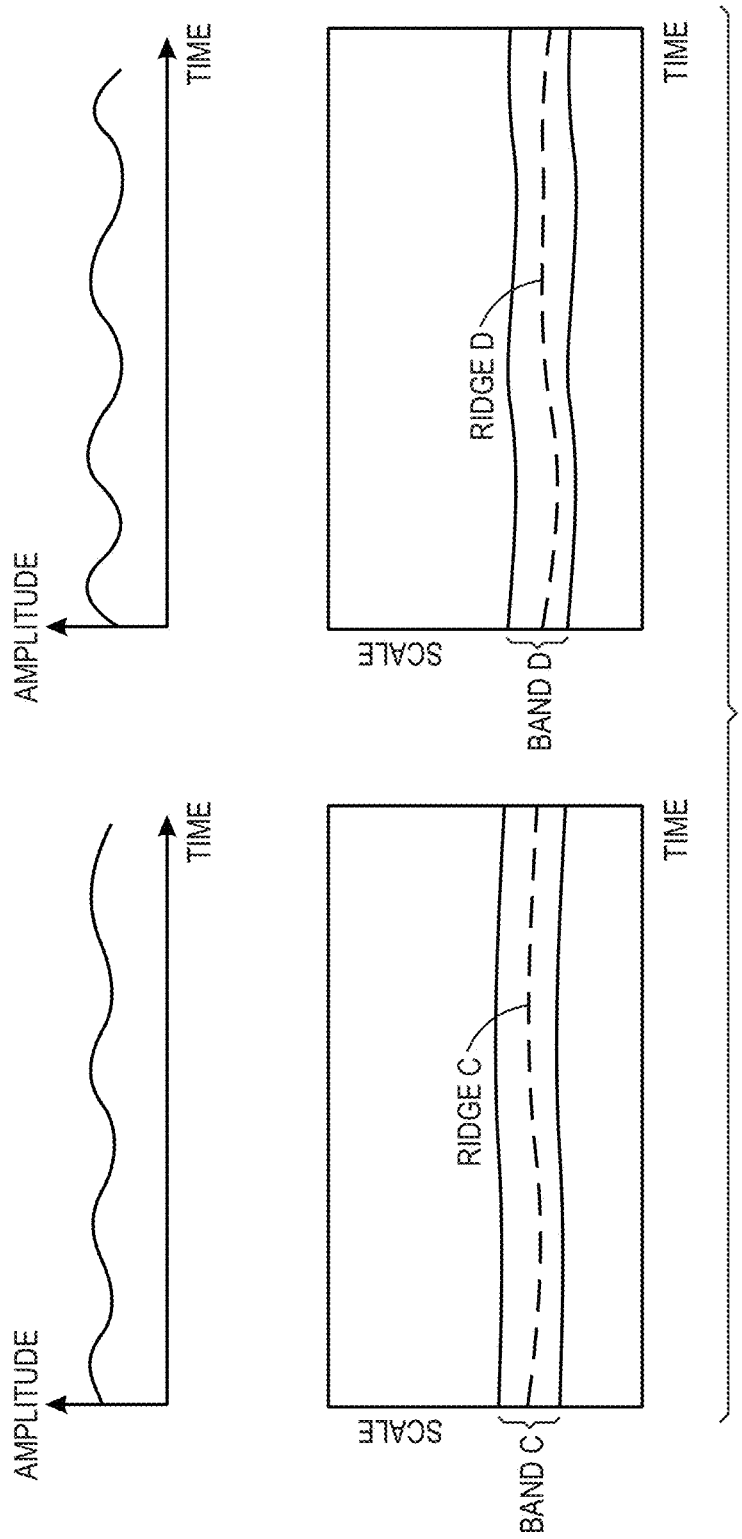

HYPOVOLEMIA DIAGNOSIS TECHNIQUE

CROSS-REFERENCE TO RELATED APPLICATIONS

This application is a division of U.S. application Ser. No. 14/509,302, filed Oct. 8, 2014, which is a continuation of U.S. application Ser. No. 13/404,402, filed Feb. 24, 2012, U.S. Pat. No. 8,880,155, the disclosures of which are hereby incorporated by reference in their entirety for all purposes.

BACKGROUND

The present disclosure relates generally to techniques for monitoring physiological parameters of a patient. Specifically, embodiments of the present disclosure relate to medical devices that are capable of providing an indication of hypovolemia.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

One physiological parameter that physicians may wish to monitor is blood fluid volume (i.e., intravascular volume). Variations from normal fluid volume in the blood may indicate a change in clinical condition or an injury. For example, hypovolemia is a state of decreased intravascular volume that may be associated with dehydration. Correct clinical assessment of hypovolemia is complex. More specifically, intravascular volume is difficult to estimate, particularly in critically ill patients. Without an accurate assessment of a patient's intravascular volume, it is difficult to predict whether a patient will respond to fluid therapy (e.g., a blood or fluid infusion) with an improvement in clinical condition, such as an increase in stroke volume and cardiac output. Accordingly, accurate assessments of intravascular volume may assist a clinician in determining whether a patient will be responsive to fluid therapy.

To this end, indicators such as the systolic blood pressure variation, pulse pressure variation, or stroke volume variation may be used to estimate intravascular volume and determine whether a patient is likely to be fluid responsive. However, these measurements tend to be invasive. For example, to obtain an accurate pulse pressure waveform from which the intravascular volume can be determined, a physician may insert an invasive arterial line.

BRIEF DESCRIPTION OF THE DRAWINGS

Advantages of the disclosed techniques may become apparent upon reading the following detailed description and upon reference to the drawings in which:

FIG. 5D shows an illustrative schematic of signals associated with a ridge in FIG. 5C and illustrative schematics of a further wavelet decomposition of these newly derived signals in accordance with an embodiment.

DETAILED DESCRIPTION OF SPECIFIC EMBODIMENTS

Figure 1:
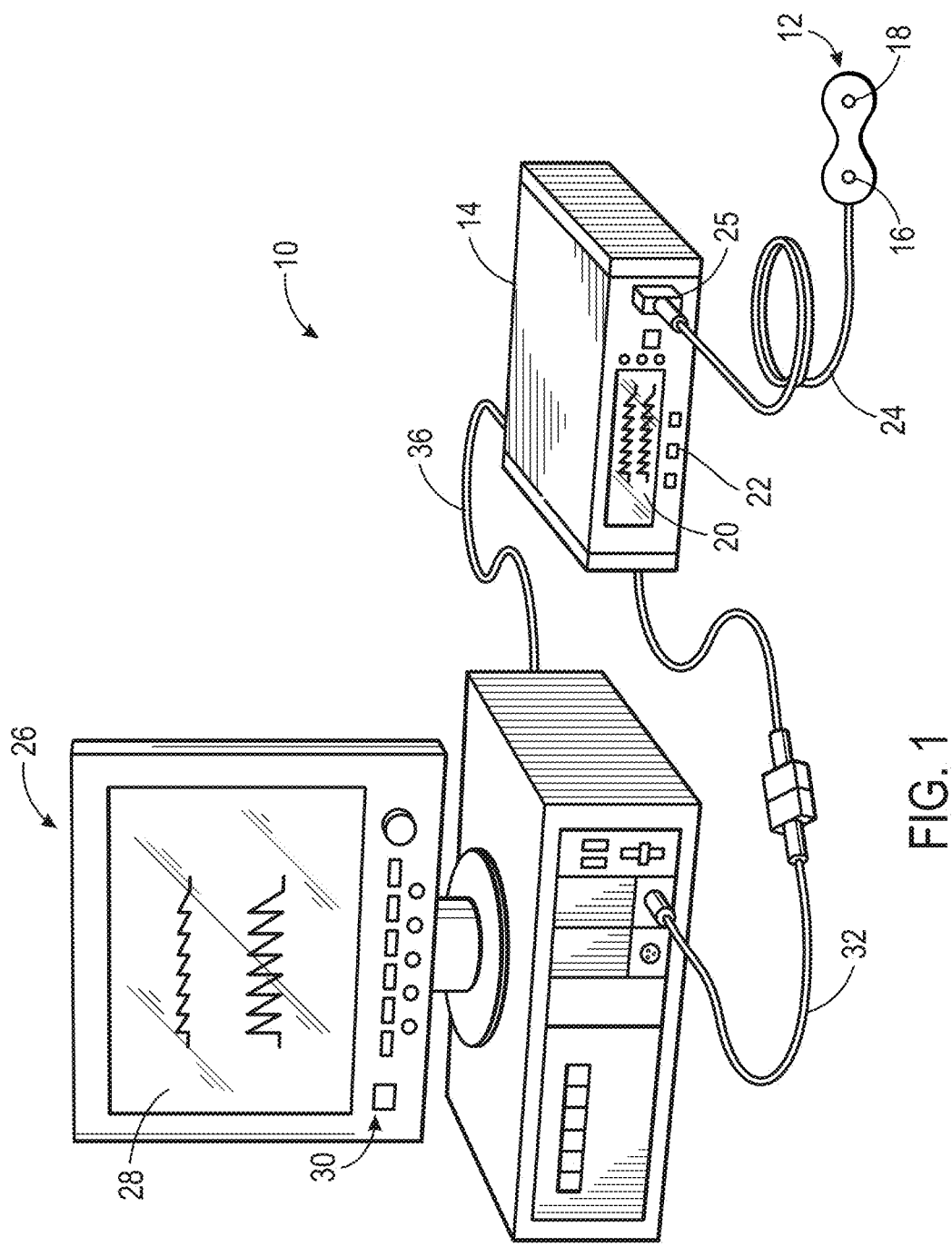
FIG. 1 is an illustration of a patient monitoring system in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Photoplethysmography is a noninvasive technique for monitoring physiological characteristics of a patient. In one example, a photoplethysmography device uses a sensor that transmits light through a patient's tissue and photoelectrically detects the absorption and/or scattering of the transmitted light in such tissue. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue or the blood oxygen saturation using various algorithms.

As provided herein, certain features of the plethysmographic waveform may be analyzed for characteristics, variations, or patterns that are linked to hypovolemia and, in certain embodiments, hypovolemic shock, e.g., loss of blood volume due to acute trauma or internal bleeding. Based on a detection of low blood volume, appropriate therapy may be administered to the patient. For example, IV or fluid therapy may be administered to a patient with hypovolemia. Additionally, the techniques provided herein may be used for monitoring surgical or post-surgical patients to detect internal bleeding or rapid blood loss.

In particular, the plethysmographic waveform includes a pulsatile AC component that may be characterized by amplitude, width, and/or an area under the curve for individual pulses. The AC component of the plethysmographic signal is representative of variations in left ventricular stroke volume during each cardiac cycle, as well as dynamic changes in the peripheral vasculature. During traumatic shock, there is a loss of blood volume that leads to reductions in left ventricular stroke volume, which in turn may be reflected as characteristic changes in the AC component of the plethysmographic waveform signal. In addition, the act of respiration results in characteristic changes in the AC component of the signal. For example, the inhalation of oxygen and exhalation of carbon dioxide are accompanied by hemodynamic changes such as beat to beat interval changes, baseline shifts, and pulse amplitude variations. Detection of these changes and analysis of their magnitude may be used to monitor the onset or presence of hypovolemic shock. In one embodiment, these waveform features may be calculated using algorithms for calculating a patient respiration rate from the plethysmographic waveform.

The changes in the plethysmographic waveform signal that are associated with hypovolemia may be detected earlier than other types of changes, including heart rate and blood pressure changes. Accordingly, the present techniques allow earlier diagnosis of hypovolemia and/or associated shock. In addition, the present techniques account for the presence of arrhythmic beats. Rather than ignoring the presence of arrhythmia, the present techniques may use the number, frequency, or type of arrhythmic beats as a factor in determining the probability of shock. For example, in one embodiment, a determination of hypovolemic shock may be based on the respiration rate pulse band, respiratory sinus arrhythmia, and baseline modulation during respiration.

With this in mind, FIG. 1 depicts an embodiment of a patient monitoring system 10 that may be used in conjunction with a plethysmographic sensor 12. Although the depicted embodiments relate to relate to photoplethysmography or pulse oximetry, the system 10 may be configured to obtain a variety of medical measurements with a suitable medical sensor. The system 10 includes the sensor 12 that is communicatively coupled to a patient monitor 14. The sensor 12 includes one or more emitters 16 and one or more detectors 18. The emitters 16 and detectors 18 of the sensor 12 are coupled to the monitor 14 via a cable 24 through a plug 25 coupled to a sensor port. Additionally, the monitor 14 includes a monitor display 20 configured to display information regarding the physiological parameters, information about the system, and/or alarm indications. The monitor 14 may include various input components 22, such as knobs, switches, keys and keypads, buttons, etc., to provide for operation and configuration of the monitor. The monitor 14 also includes a processor that may be used to execute code such as code for implementing the techniques discussed herein.

The monitor 14 may be any suitable monitor, such as a pulse oximetry monitor available from Nellcor Puritan Bennett LLC. The monitor 14 may also be capable of determining a patient's respiration rate based on the plethysmographic waveform signal. Furthermore, to upgrade conventional operation provided by the monitor 14 to provide additional functions, the monitor 14 may be coupled to a multi-parameter patient monitor 26 via a cable 32 connected to a sensor input port or via a cable 36 connected to a digital communication port, or via an RF or optical wireless link. Alternatively, the techniques provided herein may be incorporated into one or more individual modules with plug-in connectivity to the multi-parameter patient monitor 26. Such modules may include connectors that allow the calculated physiological parameters to be sent to the host multi-parameter monitor. In addition, the monitor 14, or, alternatively, the multi-parameter patient monitor 26, may be configured to calculate physiological parameters and to provide a central display 28 for the visualization of information from the monitor 14 and from other medical monitoring devices or systems. The multi-parameter monitor 26 includes a processor that may be configured to execute code. The multi-parameter monitor 26 may also include various input components 30, such as knobs, switches, keys and keypads, buttons, etc., to provide for operation and configuration of the a multi-parameter monitor 26. In addition, the monitor 14 and/or the multi-parameter monitor 26 may be connected to a network to enable the sharing of information with servers or other workstations. In certain embodiments, the sensor 12 may be a wireless sensor 12. Accordingly, the wireless sensor 12 may establish a wireless communication with the patient monitor 14 and/or the multi-parameter patient monitor 26 using any suitable wireless standard. By way of example, the wireless module may be capable of communicating using one or more of the ZigBee standard, WirelessHART standard, Bluetooth standard, IEEE 802.11x standards, or MiWi standard. In embodiments in which the sensor 12 is configured for wireless communication, the strain relief features of the cable 24 may be housed in the sensor body 34.

As provided herein, the sensor 12 may be a sensor suitable for detection of one or more physiological parameters. The sensor 12 may include optical components (e.g., one or more emitters 16 and detectors 18). In one embodiment, the sensor 12 may be configured for photo-electric detection of blood and tissue constituents. For example, the sensor 12 may include pulse oximetry sensing functionality for determining the oxygen saturation of blood as well as other parameters (e.g., respirations rate) from the plethysmographic waveform detected by the oximetry technique. An oximetry system may include a light sensor (e.g., sensor 12) that is placed at a site on a patient, typically a fingertip, toe, forehead or earlobe, or in the case of a neonate, across a foot. The sensor 12 may pass light using the emitter 16 through blood perfused tissue and photoelectrically sense the absorption of light in the tissue. For example, the monitor 14 may measure the intensity of light that is received at the light sensor as a function of time. A signal representing light intensity versus time or a mathematical manipulation of this signal (e.g., a scaled version thereof, a log taken thereof, a scaled version of a log taken thereof, etc) may be referred to as the photoplethysmograph (PPG) signal. The light intensity or the amount of light absorbed may then be used to calculate the amount of the blood constituent (e.g., oxyhemoglobin) being measured and other physiological parameters such as the pulse rate and when each individual pulse occurs. Generally, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. At least two, e.g., red and infrared (IR), wavelengths may be used because it has been observed that highly oxygenated blood will absorb relatively less red light and more infrared light than blood with a lower oxygen saturation. However, it should be understood that any appropriate wavelengths, e.g., green, etc., may be used as appropriate. Further, photoplethysmography measurements may be determined based on one, two, or three or more wavelengths of light.

Figure 2:
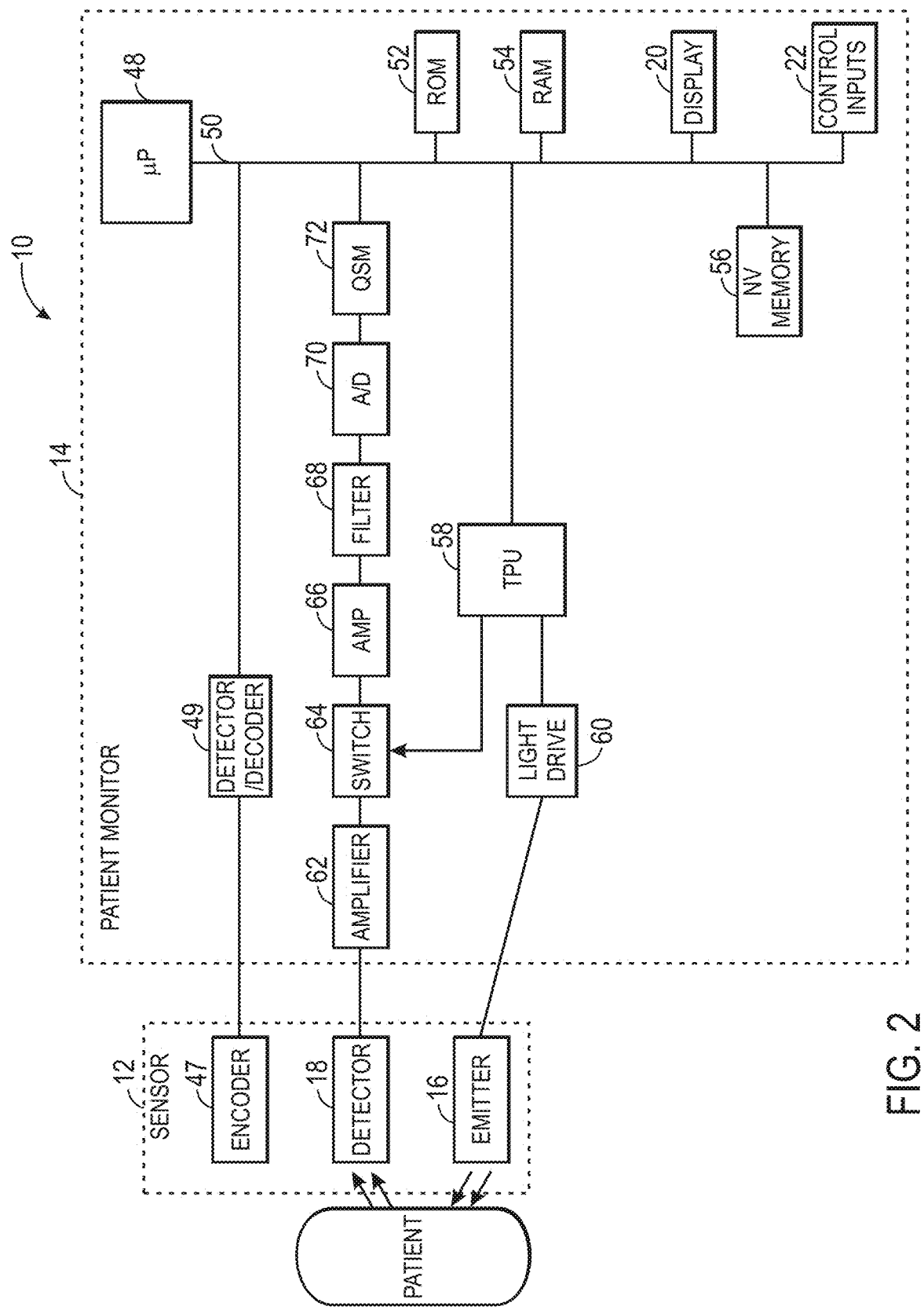
FIG. 2 is a block diagram of a patient monitor for determining hypovolemia in accordance with an embodiment.

Turning to FIG. 2, a simplified block diagram of the medical system 10 is illustrated in accordance with an embodiment. As noted, the sensor 12 may include optical components in the forms of emitters 16 and detectors 18. The emitter 16 and the detector 18 may be arranged in a reflectance or transmission-type configuration with respect to one another. However, in embodiments in which the sensor 12 is configured for use on a patient's forehead (e.g. either alone or in conjunction with a hat or headband), the emitters 16 and detectors 18 may be in a reflectance configuration. Such sensors 12 may be used for pulse oximetry or regional saturation monitoring (e.g., INVOS® monitoring). An emitter 16 may also be a light emitting diode, superluminescent light emitting diode, a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements, absorptive filters, dielectric stack filters, or interferometers. These kinds of emitters and/or detectors would typically be coupled to the sensor 12 via fiber optics. Alternatively, a sensor assembly 12 may sense light detected from the tissue is at a different wavelength from the light emitted into the tissue. Such sensors may be adapted to sense fluorescence, phosphorescence, Raman scattering, Rayleigh scattering and multiphoton events or photoacoustic effects in conjunction with the appropriate sensing elements.

In certain embodiments, the emitter 16 and detector 18 may be configured for pulse oximetry. It should be noted that the emitter 16 may be capable of emitting at least two wavelengths of light, e.g., red and infrared (IR) light, into the tissue of a patient, where the red wavelength may be between about 600 nanometers (nm) and about 700 nm, and the IR wavelength may be between about 800 nm and about 1000 nm. The emitter 16 may include a single emitting device, for example, with two LEDs, or the emitter 16 may include a plurality of emitting devices with, for example, multiple LED's at various locations. In some embodiments, the LEDs of the emitter 16 may emit three or more different wavelengths of light. Such wavelengths may include a red wavelength of between approximately 620-700 nm (e.g., 660 nm), a far red wavelength of between approximately 690-770 nm (e.g., 730 nm), and an infrared wavelength of between approximately 860-940 nm (e.g., 900 nm). Other wavelengths may include, for example, wavelengths of between approximately 500-600 nm and/or 1000-1100 nm and/or 1200-1400 nm. Regardless of the number of emitting devices, light from the emitter 16 may be used to measure, as provided herein, a risk, onset, or presence of hypovolemia. In certain embodiments, the sensor measurements may also be used for determining oxygen saturation, respiration rate, water fraction, hematocrit, or other physiologic parameters of the patient. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. In another embodiment, two emitters 16 may be configured for use in a regional saturation technique. To that end, the emitters 16 may include two light emitting diodes (LEDs) that are capable of emitting at least two wavelengths of light, e.g., red or near infrared light. In one embodiment, the LEDs emit light in the range of 600 nanometers to approximately 1000 nm. In a particular embodiment, one LED is capable of emitting light at 730 nm and the other LED is capable of emitting light at 810 nm.

In any suitable configuration of the sensor 12, the detector 18 may be an array of detector elements that may be capable of detecting light at various intensities and wavelengths. In one embodiment, light enters the detector 18 after passing through the tissue of the patient. In another embodiment, light emitted from the emitter 16 may be reflected by elements in the patient's tissue to enter the detector 18. The detector 18 may convert the received light at a given intensity, which may be directly related to the absorbance and/or reflectance of light in the tissue of the patient, into an electrical signal. That is, when more light at a certain wavelength is absorbed, less light of that wavelength is typically received from the tissue by the detector 18, and when more light at a certain wavelength is reflected, more light of that wavelength is typically received from the tissue by the detector 18. The detector 18 may receive light that has not entered the tissue to be used as a reference signal. After converting the received light to an electrical signal, the detector 18 may send the signal to the monitor 14, where physiological characteristics may be calculated based at least in part on the absorption and/or reflection of light by the tissue of the patient.

In certain embodiments, the medical sensor 12 may also include an encoder 47 that may provide signals indicative of the wavelength of one or more light sources of the emitter 16, which may allow for selection of appropriate calibration coefficients for calculating a physical parameter such as blood oxygen saturation. The encoder 47 may, for instance, be a coded resistor, EEPROM or other coding devices (such as a capacitor, inductor, PROM, RFID, parallel resident currents, or a colorimetric indicator) that may provide a signal to a microprocessor 48 related to the characteristics of the medical sensor 12 to enable the microprocessor 48 to determine the appropriate calibration characteristics of the medical sensor 12. Further, the encoder 47 may include encryption coding that prevents a disposable part of the medical sensor 12 from being recognized by a microprocessor 48 unable to decode the encryption. For example, a detector/decoder 49 may translate information from the encoder 47 before it can be properly handled by the processor 48. In some embodiments, the encoder 47 and/or the detector/decoder 48 may not be present. In some embodiments, the encrypted information held by the encoder 47 may itself be transmitted via an encrypted data protocol to the detector/decoder 49, such that the communication between 47 and 49 is secured.

Signals from the detector 18 and/or the encoder 47 may be transmitted to the monitor 14. The monitor 14 may include one or more processors 48 coupled to an internal bus 50. Also connected to the bus may be a RUM memory 52, a RAM memory 54, non-volatile memory 56, a display 20, and control inputs 22. A time processing unit (TPU) 58 may provide timing control signals to light drive circuitry 60, which controls when the emitter 16 is activated, and if multiple light sources are used, the multiplexed timing for the different light sources. TPU 58 may also control the gating-in of signals from detector 18 through a switching circuit 64. These signals are sampled at the proper time, depending at least in part upon which of multiple light sources is activated, if multiple light sources are used. The received signal from the detector 18 may be passed through one or more amplifiers (e.g., amplifiers 62 and 66), a low pass filter 68, and an analog-to-digital converter 70 for amplifying, filtering, and digitizing the electrical signals from the sensor 12. The digital data may then be stored in a queued serial module (QSM) 72, for later downloading to RAM 54 as QSM 72 fills up. In an embodiment, there may be multiple parallel paths for separate amplifiers, filters, and A/D converters for multiple light wavelengths or spectra received.

Based at least in part upon the received signals corresponding to the light received by optical components of the pulse oximetry sensor 20, microprocessor 48 may calculate a hypovolemia indicator and/or the respiration rate, oxygen saturation and/or heart rate using various algorithms, such as those employed by the Nellcor™ N-600x™ pulse oximetry monitor, which may be used in conjunction with various Nellcor™ pulse oximetry sensors, such as OxiMax™ sensors. In addition, the microprocessor 48 may calculate and/or display trend or parameter variability using various methods, such as those provided herein. These algorithms may employ certain coefficients, which may be empirically determined, and may correspond to the wavelengths of light used. The algorithms and coefficients may be stored in a RUM 52 or other suitable computer-readable storage medium and accessed and operated according to microprocessor 48 instructions. In one embodiment, the correction coefficients may be provided as a lookup table.

As provided herein, a loss or change in intravascular volume associated with hypovolemia may be determined based on changes or patterns detected in the characteristic respiratory-induced variations of the plethysmographic waveform. In particular embodiments, these changes may be assessed using algorithms for determining respiration rate and/or oxygen saturation. For example, a patient monitor 14 capable of determining a respiration rate may employ certain algorithms that assess features of the waveform including amplitude variations, baseline shifts, arrhythmic beats, and beat-to-beat variations. These features may be extracted from the algorithm calculations and used as inputs to a hypovolemia determination. In another embodiment, signal processing techniques used for processing the plethysmographic waveform signal to determine oxygen saturation may be used to assess pulse quality, changes in pulse amplitude, and/or pulse shape. Further, in particular embodiments, information about a patient's breathing cycle may also be used as an input to a hypovolemia determination.

For example, a patient's pulse amplitude may be assessed to determine if the patient is hypovolemic. For healthy patients with normal fluid status, the left ventricular stroke volume decreases as the patient breathes in. During exhalation, there is a corresponding small increase in the left ventricular stroke volume. These changes in stroke volume relate to respiratory-induced pulse amplitude variations in the plethysmographic waveform. Accordingly, changes in pulse amplitude may be used at least in part to estimate changes in stroke volume. In certain embodiments, the estimation of stroke volume may also incorporate additional factors and/or parameters, such as heart rate, vascular tone, or pulse pressure. For patients experiencing onset of hypovolemia, a relatively larger drop in stroke volume during inhalation may be observed. Similarly, a relatively larger increase in stroke volume occurs during exhalation for patients with hypovolemia. By tracking trends in pulse amplitude as correlated to a breathing cycle, early onset of hypovolemia may be detected.

Figure 3:
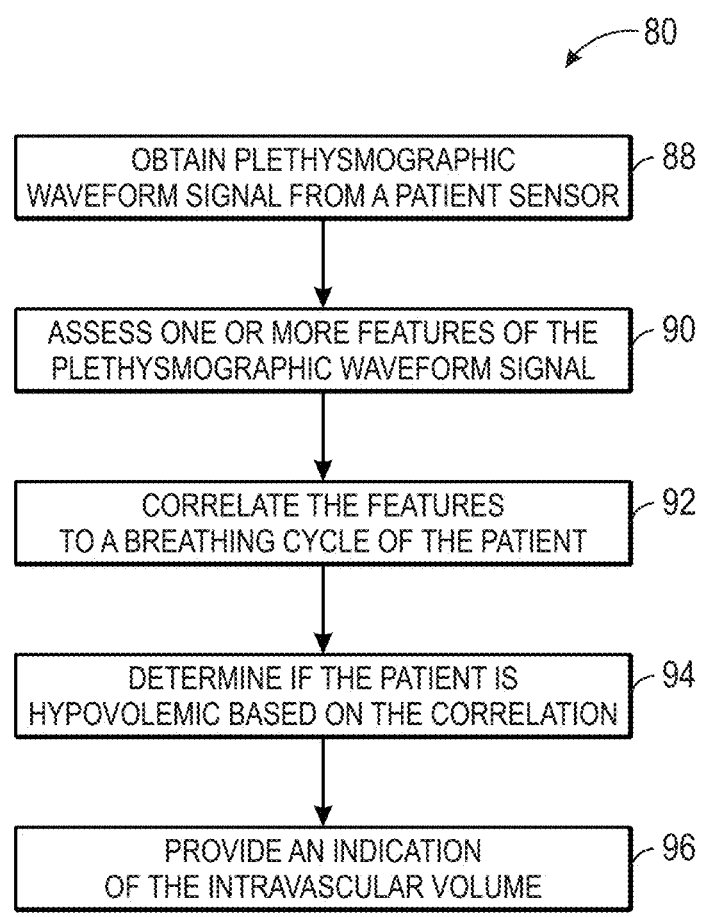
FIG. 3 is a flow diagram of a method for determining hypovolemia shock in accordance with an embodiment.

FIG. 3 is a process flow diagram illustrating a method 80 in accordance with some embodiments. The method may be performed as an automated procedure by a system, such as system 10. In addition, certain steps of the method may be performed by a processor, or a processor-based device such as a patient monitor 14 that includes instructions for implementing certain steps of the method 80. According to an embodiment, the method 80 begins with obtaining a plethysmographic waveform signal from a pulse oximetry sensor 12 at step 88.

The monitor 14 may perform assess one or more features of the plethysmographic waveform at step 90 based on the plethysmographic waveform signal obtained at step 88. At step 92, the plethysmographic waveform signal and its features are correlated to information related to a breathing cycle of a patient. The information about the breathing cycle may be determined based on an analysis of the plethysmographic waveform signal. That is, based on certain patterns associated with respiration and their effects on the plethysmographic waveform signal, the pulses may be correlated to a full breathing cycle including inspiration and exhalation or only certain portions of the breathing cycle (e.g., the inhalation and exhalation components of the signal may be extracted). Measuring respiration cycles may be performed using techniques such as those provided in U.S. Patent Publication No. 2010/0324827, which is incorporated by reference herein in its entirety for all purposes. Other inputs used in the correlation may be a patient's calculated heart rate and respiration rate. In a particular embodiment, if the patient is receiving breathing assistance, a ventilator may provide input to the system 10 to correlate the breathing cycle with the plethysmographic waveform. For patients breathing without assistance, a breathing cycle may be determined by a nasal thermistor, which measures the temperature changes that occur during inhalation and exhalation. Other techniques may involve indirect measurements of changes in body volume as a result of respiration, including transthoracic inductance, impedance plethysmography, or strain gauge measurement of thoracic circumference. Time-stamped inputs from such sensors or monitors may be provided to the monitor 14 and correlated to events in the plethysmographic waveform.

Based on patients associated with healthy fluid levels and/or hypovolemia, the monitor 14 may calculate an assessment of the patient's fluid condition, i.e., a risk of hypovolemia at step 94, and provide a display or other indication to a clinician, such as a graphical, visual, or audio representation of the intravascular volume at step 96. In one embodiment, a blood volume indicator may represent the presence of measurements, patterns, or trends in the plethysmographic waveform signal associated with normal intravascular blood volume and may include a numeric value or a green light indicated on a display or a short tone generated by a speaker associated with monitor 14. Similarly, measurements, patterns, or trends in the plethysmographic waveform signal associated with hypovolemia may trigger an alarm, which may include one or more of an audio or visual alarm indication. Further, the monitor 14 may provide a confidence metric or indicator to provide information to the clinician relating to how may parameters may have been taken into account. For example, if the indicator is takes into account the presence of arrhythmia or arrhythmic beats, the confidence may be higher than if arrhythmia is not accounted for.

In one embodiment, the alarm may be triggered if the hypovolemia indicator is substantially greater than a predetermined value, substantially less than a predetermined value, or outside of a predetermined range. The predetermined values, thresholds, and/or ranges may be empirically determined based on clinical observations of patients with normal fluid status relative to hypovolemic patients. In a particular embodiment, a hypovolemia indicator may increase if particular trends in the plethysmographic waveform are detected. One such pattern may be a trending increase in a patient's stroke volume during exhalation. Another such trend may be a trending decrease in a patient's stroke volume during inhalation. These two trends in combination with one another may also be used to increase confidence for the hypovolemia indicator. Further, trending increases or decreases may be assessed over one or more breathing cycles. For example, maintaining an increase or decrease in a trending value over multiple breath cycles may also increase confidence for the hypovolemia indicator. The trend values may be relative to previously assessed values in the patient or may be relative to empirically-determined cutoff values. In one embodiment, the monitor 14 may employ a truth table in which hypovolemia is indicated if both trends are present for a minimum time period. In another example, each incidence of a change in stroke volume outside of a normal threshold may be added to a counter, which may trigger an alarm when the counter reaches a minimum count.

In one embodiment, the disclosed techniques for monitoring hypovolemia may be used during a surgical procedure. In such an embodiment, a plurality of baseline measurements of the characteristics of the plethysmographic waveform may be recorded, for example over a five or ten minute period prior to the surgery. These baseline measurements may then be used to compute a baseline value of, for example, pulse amplitude during inhalation and exhalation. During and post-surgery, any trends of pulse amplitude (or any other suitable characteristic of the plethysmographic waveform) that are associated with hypovolemia may be assessed. As noted, a trend of increasing pulse amplitude during exhalation relative to a baseline or pre-surgery level may be indicative of hypovolemia. Because hypovolemia may be a precursor to hypovolemic shock, early detection may lead to timely fluid treatment and improved surgical outcomes.

Figure 4:
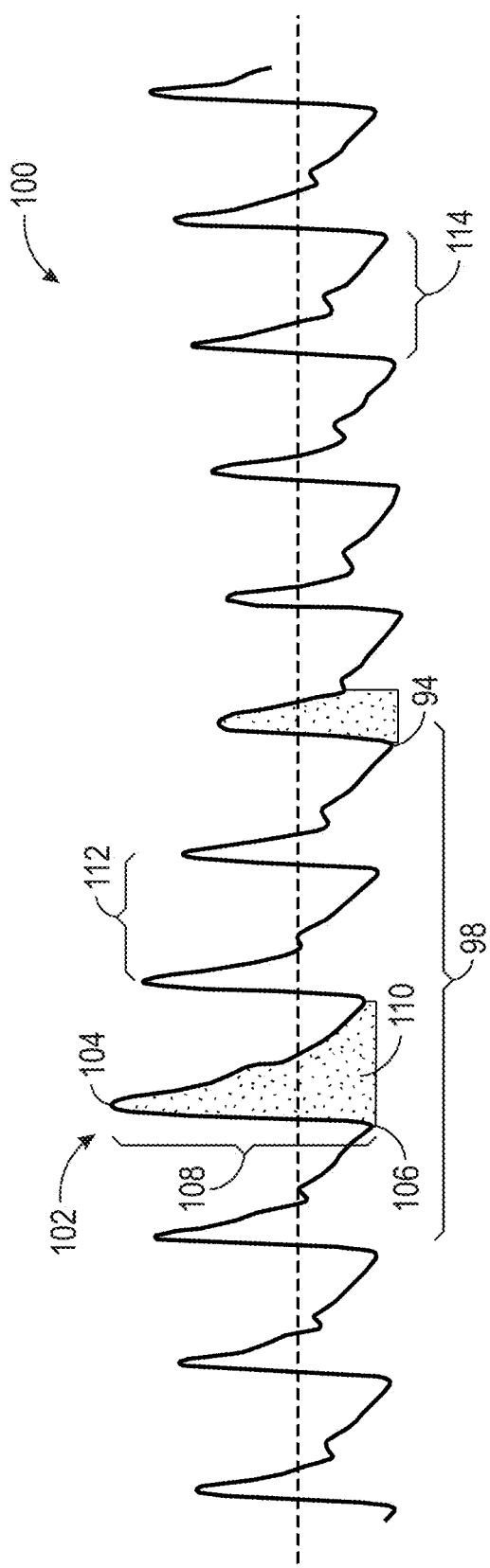
FIG. 4 is an illustration of a plethysmographic waveform signal.

FIG. 4 illustrates particular features or characteristics of a plethysmographic waveform 100 that may be assessed in determining if a patient is at risk of developing hypovolemia. An individual peak 102 may be characterized by its peak 104 and its trough 106. In addition, the absolute distance 108 between the peak 104 and the trough 106 and the area under the curve 110 may be assessed. The plethysmographic waveform may also be assessed by its peak-to-peak variation 112, trough-to-trough variation 114, or a change in absolute distance 108 from beat-to-beat. In one embodiment, a pulse amplitude may be assessed as the absolute distance 108. In addition, a time window 116 for assessing changes or trends may be selected according to the desired monitoring parameters. For example, an operator may increase the size of the window 116 from 10 seconds to 30 seconds to capture more data. The monitor 14 may provide rolling updates as the window 116 moves forward in time.

The plethysmographic waveform 100 is pulsatile and reflects hemodynamic properties, which may be used to determine a patient's blood oxygen saturation as well as heart rate. In addition, the plethysmographic waveform may be used to determine a patient's respiration rate. In one embodiment, the respiratory rate may be determined by analyzing a wavelet transformed plethysmographic signal. Information derived from the transform of the plethysmographic signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \quad (1)$$

where $\psi^*(t)$ is the complex conjugate of the wavelet function $\psi(t)$, a is the dilation parameter of the wavelet and b is the location parameter of the wavelet. The transform given by equation (1) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \quad (2)$$

where '||' is the modulus operator. The scalogram may be rescaled for useful purposes. One common rescaling is defined as $$S_R(a, b) = \frac{|T(a, b)|^2}{a} \quad (3)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane is labeled a "maxima ridge".

For implementations involving fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by √(a).

In the discussion of the techniques herein, the "scalogram" may be taken to include all suitable forms of rescaling including, but not limited to, the original unsealed wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (4)$$

where $f_c$ the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (5)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (6)$$

This wavelet is a complex wave within a scaled Gaussian envelope. While both definitions of the Morlet wavelet are included herein, the function of equation (6) is not strictly a wavelet as it has a non-zero mean (i.e., the zero frequency term of its corresponding energy spectrum is non-zero). However, it will be recognized by those skilled in the art that equation (6) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of plethysmographic signals may be used to provide clinically useful information within a medical device.

Figures 5A, 5B:
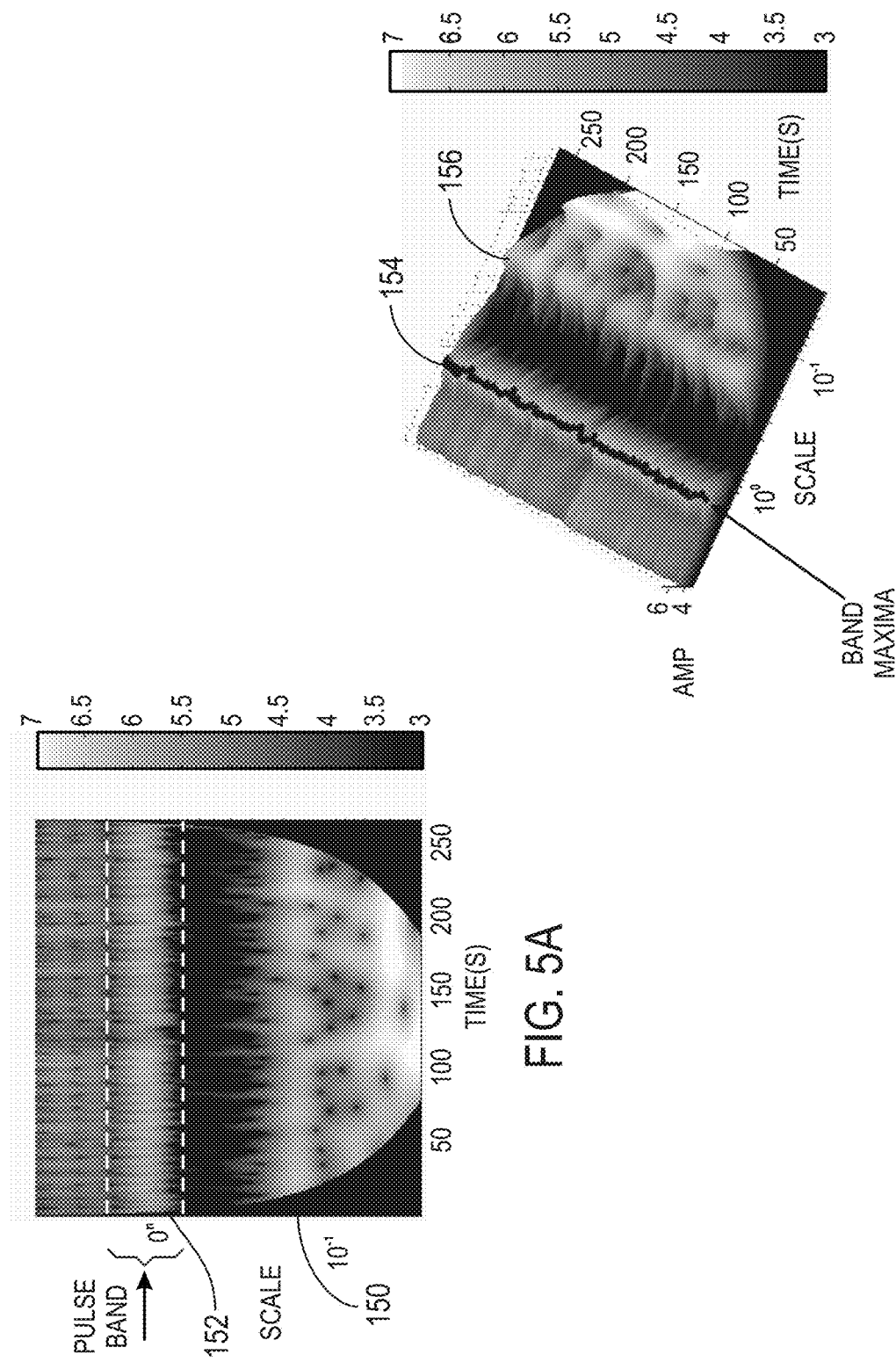
FIGS. 5A and 5B show illustrative views of a scalogram derived from a plethysmographic signal in accordance with an embodiment.

Pertinent repeating features in a signal give rise to a time-scale band in wavelet space or a rescaled wavelet space. For example, the pulse component of a plethysmographic signal produces a dominant band in wavelet space at or around the pulse frequency. FIGS. 5A and B show two views of an illustrative scalogram 150 derived from a plethysmographic signal, according to an embodiment. The figures show an example of the band 152 caused by the pulse component in such a signal. The pulse band is located between the dashed lines in the plot of FIG. 5A. The band is formed from a series of dominant coalescing features across the scalogram. This can be clearly, seen as a raised band across the transform surface in FIG. 5B located within the region of scales indicated by the arrow in the plot (corresponding to 60 beats per minute). The maximum of this band with respect to scale is the ridge. The locus of the ridge is shown as a black curve on top of the band in FIG. 5B. By employing a suitable rescaling of the scalogram, such as that given in equation (3), the ridges found in wavelet space may be related to the instantaneous frequency of the signal. In this way, the pulse rate may be obtained from the plethysmographic signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 5C:
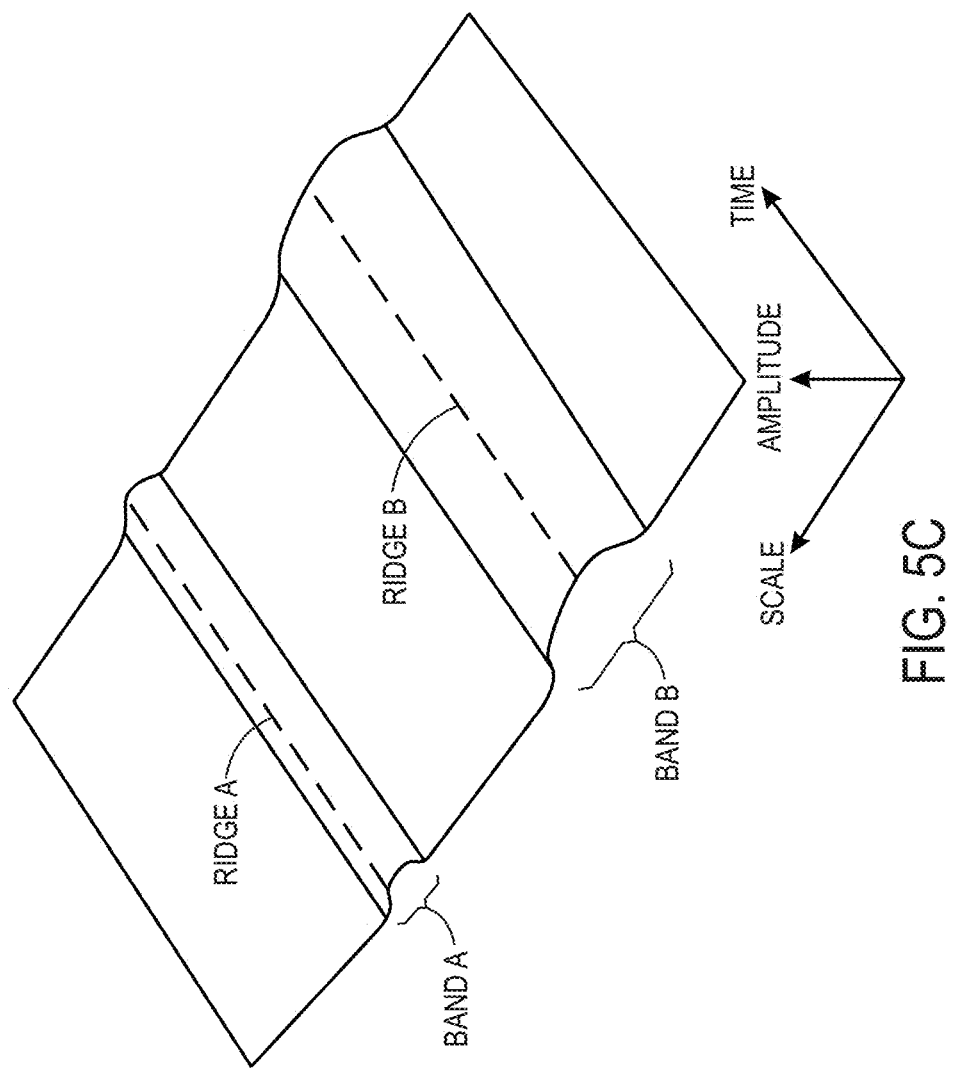
FIG. 5C shows an illustrative scalogram derived from a signal containing two pertinent components in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 5C shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band." In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude and time-scale planes, respectively. The top plots of FIG. 5D show a schematic of the RAP and RSP signals associated with ridge A in FIG. 5C. Below these RAP and RSP signals are schematics of a further wavelet decomposition of these newly derived signals. This secondary wavelet decomposition allows for information in the region of band B in FIG. 5C to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 5C) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \tag{7}$$

which may also be written as:

$$x(t) = \frac{1}{C_g} \int_{-\infty}^{\infty} \int_0^{\infty} T(a,b) \psi_{a,b}(t) \frac{da\,db}{a^2} \tag{8}$$

where $C_g$ is a scalar value known as the admissibility constant. It is wavelet type dependent and may be calculated from:

$$C_g = \int_0^{\infty} \frac{|\hat{\psi}(f)|^2}{f} df \tag{9}$$

A continuous wavelet transform may be used to obtain characteristic metrics of the respiratory components in a plethysmographic signal, which are, in turn, correlated with fluid responsiveness. In an embodiment, at least one suitable region, such as a ridge or a band of the scalogram may be analyzed to determine a level of fluid responsiveness in a patient. For example, the amplitude modulation of a pulse band ridge, such as pulse band ridge 154 in FIG. 5B, of the scalogram may be analyzed to determine information related to fluid responsiveness. Changes in the amplitude modulation of the plethysmographic signal correlate with changes in the level of fluid responsiveness.

The pulse band ridge manifests itself in the scalogram generated from the wavelet transform. The amplitude modulation of the plethysmographic signal may be taken from the amplitude modulation of pulse band ridge. By measuring the amplitude variation of puke band ridge, the local pulse modulation of the plethysmographic signal may be extracted. Thus, the level of fluid responsiveness may be captured by the relative pulse amplitude modulation (RPAM), which correlates the amplitude modulation of the plethysmographic signal to the level of fluid responsiveness. Higher values of RPAM may indicate greater levels of fluid responsiveness of a patient. The RPAM may be approximated by the properly scaled ratio A/M, where A may be peak-to-peak amplitude modulation of the pulse band ridge and M may be a baseline signal such as mean value of the pulse band ridge. The ratio A/M may be expressed as a percentage.

Other ratios or mathematical expressions may be used to define the RPAM. For example, A may be the standard deviation of the amplitude modulation of pulse band ridge, the median absolute value of the amplitude modulation of pulse band ridge, any other suitable metric that expresses the amplitude modulation of pulse band ridge to define the RPAM, or any combination thereof. In addition, other characteristic baselines signals or features may be used for M when defining the RPAM. For example, M may be the lower bound of the signal interpolated from the troughs of pulse band ridge, the upper bound of the signal interpolated from the peaks of pulse band ridge, any other suitable characteristic baseline signal, or any combination thereof.

In an embodiment, the carrier wave amplitude of the plethysmographic signal may be analyzed to determine information related to fluid responsiveness. Changes in the amplitude of the carrier wave during a breathing cycle correlate with changes in the level of fluid responsiveness. For example, the carrier wave amplitude may be extracted from the amplitude of the breathing band, such as breathing band 156 in FIG. 5B, of the scalogram. The carrier wave may be indicative of venous return, and the breathing band manifests itself in the scalogram generated from the wavelet transform.

In another embodiment, the amplitude of the respiratory sinus arrhythmia (RSA) component of the plethysmographic signal may be analyzed to determine information related to fluid responsiveness. Changes in the amplitude of the RSA component correlate with changes in the level of fluid responsiveness. For example, the RSA component may be derived from the pulse band ridge, such as pulse band ridge 154 in FIG. 5(b), of the scalogram. Further, any band in the transform space indicative of pulse period may provide information for measuring RSA, such as a band at a scale above that of the pulse band, which, though of lower amplitude, may clearly indicate RSA. The amplitude modulation of the RSA may correlate with the amplitude modulation of the pulse band ridge. By measuring the amplitude variation of the pulse band ridge, the local modulation of the RSA waveform may be extracted. The RSA occurs naturally in the variation in the periodicity of the heart beat timing over the respiration cycle. The amplitude modulation of other components of the scalogram indicative of pulse period may be used to measure RSA in place of or in addition to the amplitude modulation of the pulse band ridge.

Figure 6:
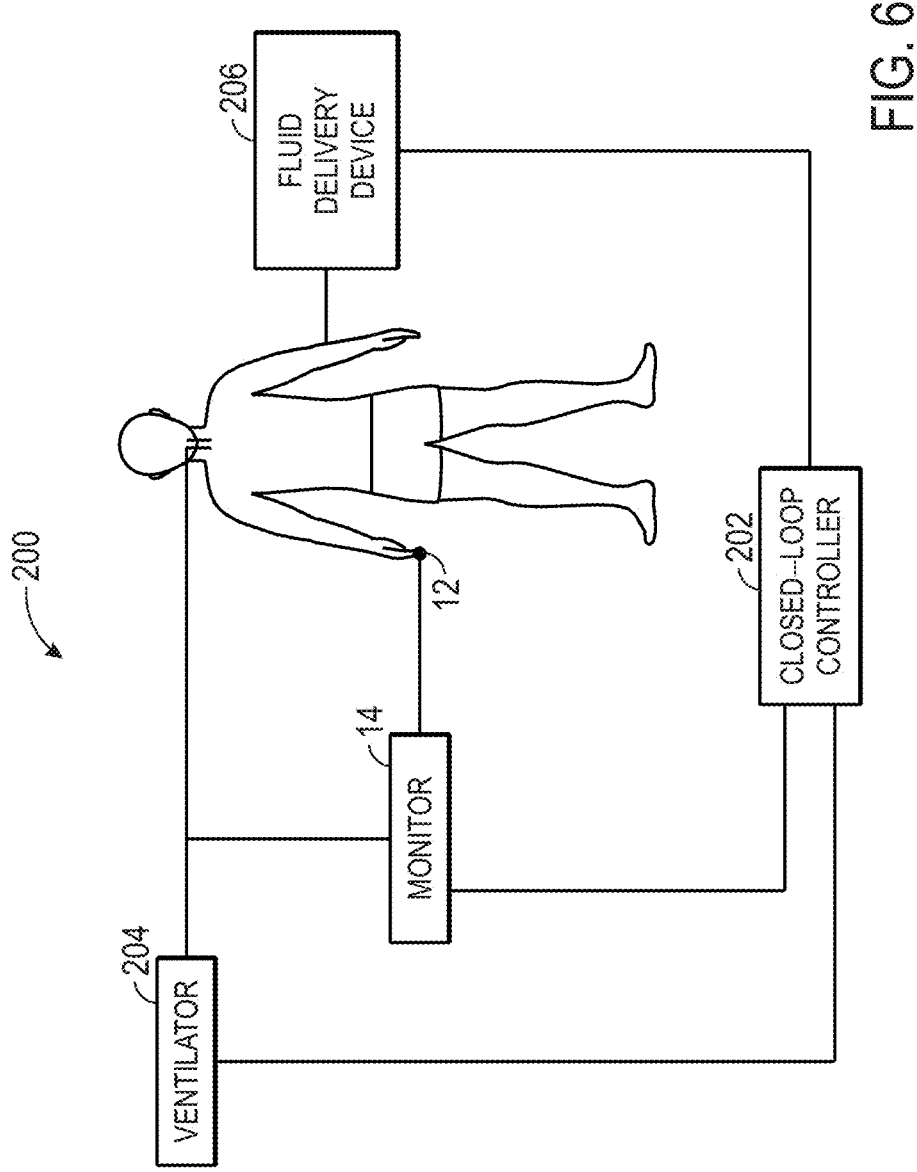
FIG. 6 is a block diagram of a closed-loop ventilation system for administering a fluid therapy in accordance with an embodiment.

In other embodiments, a patient respiratory system 200 may operate under closed-loop control to provide to delivery of a fluid therapy (e.g., saline, blood, or other fluid) to a patient. FIG. 6 shows a system 200 under control of a primary controller 202 that may include a closed-loop controller that cooperates with a monitor 14 to control delivery of fluid therapy to the patient. The primary controller 202 may receive input from the monitor 14. The controller may also receive input from a ventilator 204 or other device for determining a breathing cycle of a patient. Based on the plethysmographic waveform signal from the sensor 12, the monitor 14 may determine a hypovolemia risk, such as a numeric indicator, based on one or more features of the plethysmographic waveform. The assessment of hypovolemia risk may be used by the controller 202 to control the fluid delivery device 206. It should be understood that while FIG. 6 depicts the controller 202 and the monitor 14 as separate devices, the monitoring functions of monitor 14 and the controller functions of controller 202 may be incorporated into a single device in embodiments.

For example, the controller 202 may receive a request for increased fluid from the monitor 14 when the monitor determines that the patient is at risk for hypovolemia. The fluid delivery device 206 may include a peristaltic pump or other type of pump attached to an automatic intravenous line to achieve the desired delivery rate of the fluid to the patient. To control the rate at which the pump infuses the fluid, the speed of the pump may be controlled by the closed-loop controller 202. The monitor 14 may continue to assess the patient's fluid condition during the fluid therapy. For example, if the plethysmographic waveform features show a change in trend or absolute value that indicates that the risk of hypovolemia is reduced, the controller 202 may slow or stop delivery of fluid from the fluid delivery device 206. If the monitor 14 determines that the patient has not responded to fluid therapy, i.e., the analyzed plethysmographic waveform features are consistent with hypovolemia, the controller 202 may generate a signal notifying a caregiver of prolonged hypovolemia.

While the disclosure may be susceptible to various modifications and alternative forms, specific embodiments have been shown by way of example in the drawings and will be described in detail herein. However, it should be understood that the disclosure is not intended to be limited to the particular forms disclosed. Rather, the disclosure is to cover all modifications, equivalents and alternatives falling within the spirit and scope of the disclosure as defined by the following appended claims. Further, it should be understood that elements of the disclosed embodiments may be combined or exchanged with one another.

What is claimed is:

1. A method comprising:
receiving, by a processor, a photoplethysmographic waveform signal from a sensor applied to a patient;
determining, by the processor, a stroke volume over time for the patient based on one or more features of the photoplethysmographic waveform signal;
correlating, by the processor, the stroke volume in time to an exhalation portion of a respiratory cycle of the patient; and
determining, by the processor, that the patient is at risk of developing hypovolemia based on an increase in the stroke volume during the exhalation portion of the respiratory cycle relative to a first range or threshold.

2. The method of claim 1, wherein determining that the patient is at risk of developing hypovolemia comprises determining an increased risk based on a trend of an increase in the stroke volume during the exhalation portion of the respiratory cycle.

3. The method of claim 1, wherein determining that the patient is at risk of developing hypovolemia comprises determining a reduced risk based on a relative decrease in the stroke volume during the exhalation portion of the respiratory cycle after administration of fluid therapy.

4. The method of claim 1, further comprising triggering, by the processor, an alarm in response to determining that the patient is at risk of developing hypovolemia.

5. The method of claim 1, further comprising:
correlating, by the processor, the stroke volume in time to an inhalation portion of the respiratory cycle of the patient;
determining, by the processor, a first trend of an increase in the stroke volume during the exhalation portion of the respiratory cycle relative to the first range or threshold; and
determining, by the processor, a second trend of a decrease in the stroke volume during the inhalation portion of the respiratory cycle relative to a second range or threshold,
wherein determining that the patient is at risk of developing hypovolemia comprises determining that the patient is at risk of developing hypovolemia based on a truth table, wherein the truth table comprises an indication of developing hypovolemia if the first and the second trend are present for a threshold time period.

6. The method of claim 1, wherein determining that the patient is at risk of developing hypovolemia comprises counting a number of times of the increase in the stroke volume during the exhalation portion of the respiratory cycle relative to the first range or threshold.

7. The method of claim 1, further comprising:
analyzing, by the processor, the stroke volume over time after fluid therapy has been administered to the patient; and
determining, by the processor, that a blood volume of the patient has changed after administration of the fluid therapy.

8. The method of claim 1, wherein the one or more features of the photoplethysmographic waveform signal comprise a pulse amplitude.

9. The method of claim 1, wherein the one or more features of the photoplethysmographic waveform signal comprises at least one of a baseline shift, arrhythmic beats, a beat-to-beat variation, an area under a curve, or a pulse shape.

10. A method comprising:
receiving, by a processor, a photoplethysmographic waveform signal from a sensor applied to a patient;
determining, by the processor, a stroke volume of the patient over time based on one or more features of the photoplethysmographic waveform signal;
correlating in time, by the processor, the stroke volume to an exhalation portion of a respiratory cycle of the patient;
determining, by the processor, a baseline value of the stroke volume over a period of time;
determining, by the processor, a trend of the stroke volume during the exhalation portion of the respiratory cycle, wherein the trend is indicative of a trending change in the stroke volume relative to the baseline value, and wherein the trending change comprises an increase in the stroke volume relative to the baseline value during the exhalation portion of the respiratory cycle that is greater than a range or threshold; and
determining, by the processor, a risk of hypovolemia based on a comparison of the trend to the baseline value.

11. The method of claim 10, wherein determining the risk of hypovolemia comprises determining an increased risk based on the trend of the increase in the stroke volume during the exhalation portion of the respiratory cycle.

12. The method of claim 10, wherein determining the stroke volume over time comprises determining the stroke volume over time in a time window, wherein the time window advances with respect to time.

13. The method of claim 10, further comprising extracting, by the processor, one or more portions of the photoplethysmographic waveform signal correlated in time to the exhalation portion of the respiratory cycle, and wherein determining the trend of the stroke volume during the exhalation portion of the respiratory cycle comprises determining the trend of the stroke volume in the extracted one or more portions of the photoplethysmographic waveform signal correlated in time to the exhalation portion of the respiratory cycle.

14. The method of claim 10, wherein determining the risk of hypovolemia comprises determining a hypovolemia indicator is greater than a predetermined threshold value or outside of a predetermined range, the method further comprising triggering, by the processor, an alarm in response to determining the hypovolemia indicator is greater than the predetermined threshold value or outside of the predetermined range.

15. The method of claim 10, further comprising displaying an indicator related to the risk of hypovolemia on a display.

16. A monitor comprising:
an input configured to be coupled to a sensor applied to a patient and to receive a photoplethysmographic waveform signal from the sensor;
a processor; and
a memory storing instructions that, when executed on the processor, are configured to cause the processor to:
determine a stroke volume over time for the patient based on one or more features of the photoplethysmographic waveform signal;
correlate the stroke volume in time to an exhalation portion of a respiratory cycle of the patient; and
determine a risk of hypovolemia based on an increase in the stroke volume during the exhalation portion of the respiratory cycle relative to a range or threshold.

17. The monitor of claim 16, wherein the instructions that cause the processor to determine the risk of hypovolemia, cause the processor to determine the risk of hypovolemia based on the increase in the stroke volume during the exhalation portion of the respiratory cycle relative to a baseline stroke volume value that is greater than the range or threshold.

18. The monitor of claim 16, wherein the instructions that cause the processor to determine the risk of hypovolemia, cause the processor to determine a trend of the increase in the stroke volume over time during the exhalation portion of the respiratory cycle relative to the range or threshold.

19. The monitor of claim 18, wherein the instructions further cause the processor to:
correlate the stroke volume in time to an inhalation portion of the respiratory cycle of the patient;
determine an additional trend of a decrease in the stroke volume during the inhalation portion of the respiratory cycle relative to an additional range or threshold; and
determine the risk of developing hypovolemia based on the trend and the additional trend.

20. The monitor of claim 19, wherein the instructions that cause the processor to determine the risk of hypovolemia cause the processor to compare the trend and the additional trend to a truth table, wherein the truth table comprises an indication of developing hypovolemia based on a determination that the trend and the additional trend are present for a threshold time period.

21. The monitor of claim 16, wherein the instructions further cause the processor to:
analyze the stroke volume over time after fluid therapy has been administered to the patient; and
determine that a blood volume of the patient has changed after administration of fluid therapy.

22. The monitor of claim 16, wherein the one or more features of the photoplethysmographic waveform signal comprises a pulse amplitude.

23. The monitor of claim 16, wherein the one or more features of the photoplethysmographic waveform signal comprises at least one of a baseline shift, arrhythmic beats, a beat-to-beat variation, an area under a curve, or a pulse shape.

24. The monitor of claim 16, wherein the range or threshold is empirically determined based on clinical observations of patients with normal fluid status relative to hypovolemic patients.

* * * * *